US012616433B2

(12) United States Patent
Radicke et al.

(10) Patent No.: US 12,616,433 B2
(45) Date of Patent: May 5, 2026

(54) MAMMOGRAPHY SYSTEM HAVING A PROTECTIVE UNIT

(71) Applicant: Siemens Healthineers AG, Forchheim (DE)

(72) Inventors: Marcus Radicke, Veitsbronn (DE); Jutta Speitel, Erlangen (DE); Stephanie Goettler, Neumarkt (DE); Ralf Nanke, Neunkirchen am Brand (DE); Lukas Eller, Forchheim (DE); Tom Weidner, Erlangen (DE); Juliane Muench, Moehrendorf (DE); Andreas Limmer, Fuerth (DE)

(73) Assignee: SIEMENS HEALTHINERS AG, Forchheim (DE)

( * ) Notice: Subject to any disclaimer, the term of this patent is extended or adjusted under 35 U.S.C. 154(b) by 173 days.

(21) Appl. No.: 18/695,506

(22) PCT Filed: Sep. 23, 2022

(86) PCT No.: PCT/EP2022/076462
§ 371 (c)(1),
(2) Date: Mar. 26, 2024

(87) PCT Pub. No.: WO2023/052252
PCT Pub. Date: Apr. 6, 2023

(65) Prior Publication Data
US 2024/0407746 A1     Dec. 12, 2024

(30) Foreign Application Priority Data
Sep. 30, 2021   (EP) ..................................... 21200287
Sep. 22, 2022   (EP) ..................................... 22197199

(51) Int. Cl.
*A61B 6/00*          (2024.01)
*A61B 6/04*          (2006.01)
(Continued)

(52) U.S. Cl.
CPC ............ *A61B 6/502* (2013.01); *A61B 6/0414* (2013.01); *A61B 6/102* (2013.01); *A61B 6/107* (2013.01); *A61B 6/547* (2013.01)

(58) Field of Classification Search
CPC ........ A61B 6/025; A61B 6/0414; A61B 6/502
See application file for complete search history.

(56) References Cited

U.S. PATENT DOCUMENTS 12,396,693 B2 *   8/2025   Wolff .................... A61B 6/4035
2007/0058774 A1   3/2007   Ramsauer
(Continued)

FOREIGN PATENT DOCUMENTS

DE      102006007833 A1     8/2006
DE      102013223390 A1     5/2015
(Continued)

OTHER PUBLICATIONS

T. Weidner, "Mammographiesystem mit neuartiger Kopfstütze." 2020.

*Primary Examiner* — Dani Fox
(74) *Attorney, Agent, or Firm* — Harness, Dickey & Pierce, P.L.C.

(57) ABSTRACT

The invention relates to a mammography system having a stand unit for locating the mammography system on the floor; an L-shaped source unit, the L-shaped source unit including an arm connected to an X-ray detector in a rotatably mounted manner on a front face of the stand unit, and another arm of the L-shaped source unit protrudes substantially perpendicularly, an X-ray source being located at an end of the source unit remote from the stand unit; and a substantially U-shaped protective unit.

19 Claims, 4 Drawing Sheets

(51) Int. Cl.
    *A61B 6/10*         (2006.01)
    *A61B 6/50*         (2024.01)

(56)           References Cited

U.S. PATENT DOCUMENTS

2010/0183119 A1 *  7/2010  Ludwig .................. A61B 6/025
                                            378/37
2012/0051500 A1    3/2012  Johansson et al.
2016/0256125 A1 *  9/2016  Smith  .................. A61B 6/5223

FOREIGN PATENT DOCUMENTS

EP            2679157 A1   1/2014
WO    WO 2009047054 A1   4/2009
WO    WO 2020069031 A1   4/2020

* cited by examiner

MAMMOGRAPHY SYSTEM HAVING A PROTECTIVE UNIT

PRIORITY STATEMENT

This application is the national phase under 35 U.S.C. § 371 of PCT International Application No. PCT/EP2022/076462 which has an International filing date of Sep. 23, 2022, which designated the United States of America, which claims priority under 35 U.S.C. § 119 to European Patent Application No. 21200287.7, filed Sep. 30, 2021 and European Patent Application No. 22197199.7, filed Sep. 22, 2022, the entire contents of each of which are hereby incorporated herein by reference.

FIELD

One or more example embodiments of the present invention relates to a mammography system having a protective unit that protects the head of the object under examination from collisions with the X-ray source.

RELATED ART

In X-ray based breast imaging, the patient is normally examined standing up. In this process, the breast is placed on an X-ray detector; opposite the detector is an X-ray tube which, in the case of a 3D acquisition (tomosynthesis), is deflected in relation to the detector normal. In modern devices, the X-ray tube moves at a speed of over 2° per second. The X-ray tube is positioned at a distance of about 650 mm from the detector, which means that for many patients the tube movement takes place at head height. The distance between moving tube and patient head is only a few centimeters because of the necessary positioning. Therefore a collision with the moving X-ray tube is theoretically possible and should be ruled out as far as possible by the system hardware and software.

DE 10 2006 007 833 A1 discloses an imaging device such as a mammography device, for instance, for producing radiographic images and/or images of an object that have been recreated by tomosynthesis. This device contains an X-ray source, a breast support located between the X-ray source and an image receiver, wherein the X-ray source is located in a head element that is fastened on a rotatably mounted arm carried by a first carriage, which slides on a pillar, and at least one radiotransparent compression plate, which is located between the radiation source and the breast support and fastened on a second carriage for sliding in order to compress the breast of a patient. The device has at least one shield for protecting the head or neck of the patient, which shield can be held in a fixed position in relation to the head or neck of the patient, between the path of the X-ray source and the head or neck of the patient during a tomographic acquisition, in which the X-ray source is rotated, or between the X-ray source and the head or neck of the patient when radiographic images are to be acquired, it being possible to retract or remove the shield.

SUMMARY

One or more example embodiments of the present invention defines a mammography system that allows comfortable protection of the patient.

The object is achieved according to the invention by a mammography system as claimed in claim 1.

BRIEF DESCRIPTION OF THE DRAWINGS

Exemplary embodiments of the invention are described in greater detail below with reference to drawings, in which.

DETAILED DESCRIPTION

Figure 1:
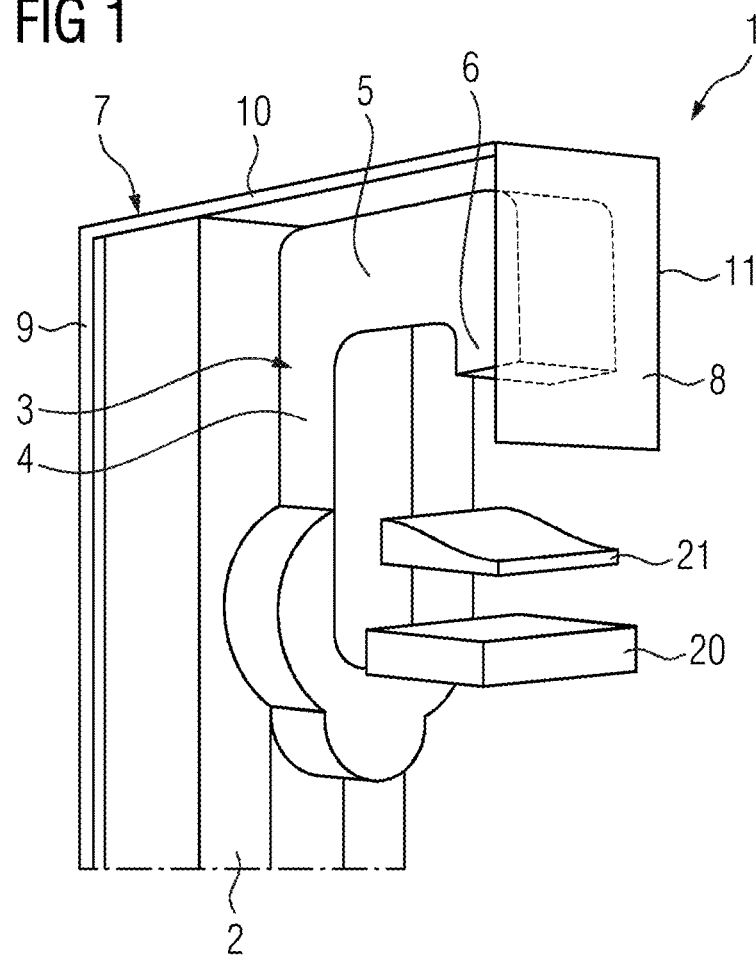
FIG. 1 shows schematically a representation of an X-ray system according to the invention in a first embodiment.

In particular, one or more example embodiments of the present invention can relate to a mammography system, having:

a stand unit for locating the mammography system on the floor;

an L-shaped source unit, one arm of which is connected to an X-ray detector in a rotatably mounted manner on a front face of the stand unit, and the other arm protrudes substantially perpendicularly, with the result that an X-ray source is located at the end of the source unit remote from the stand element or the stand unit;

a substantially U-shaped protective unit, the first arm of which is attached to the stand unit, preferably to a rear face of the stand unit, in a rotatably mounted manner such that it can rotate independently of the source unit, the second arm extends along the top face of the source unit in a first operating state, and the third arm has, at the end of the protective unit remote from the stand element, a protective shield for supporting the patient's head.

The mammography system is designed to be located and fastened on the floor, in particular of an examination room. The stand unit stands on the floor. On the stand unit is located an L-shaped source unit. The source unit is connected to the stand unit in a rotatably mounted manner so as to facilitate full-field digital mammography acquisitions from different acquisition angles, for instance craniocaudal or mediolateral oblique, and tomosynthesis acquisitions. The source unit is L-shaped. One arm runs substantially parallel to the front of the stand unit and comprises the rotatably mounted connection to the stand unit. Also located on the stand unit is an X-ray detector, which is likewise designed to be rotatably mounted, namely with respect to both the source unit and the stand unit. Hence the source unit and the X-ray detector can be rotated independently of one another with respect to the stand unit. The breast can be arranged in particular on a housing surface of the X-ray detector. The breast can be arranged as an object under examination between the X-ray source and the X-ray detector. The X-ray detector can be stationary in particular during the X-ray acquisition. For a full-field digital mammography acquisition, the X-ray source can be located opposite the X-ray detector so that the central ray of the X-ray source strikes the detection surface of the X-ray detector at right angles. For a tomosynthesis acquisition, the X-ray source can be rotated via the source unit, in particular in an angle range of 15 to 50 degrees. For the central projection, the central ray can strike the detection surface at right angles.

The protective unit is U-shaped. The protective unit comprises three arms. The first arm is attached to the stand unit in a rotatably mounted manner such that it can rotate independently of the source unit. The first arm is preferably attached to a rear face of the stand unit in a rotatably or pivotably mounted manner. The second arm extends along the top face of the source unit in a first operating state. Thus the first and second arms can follow the shape of the rear face of the stand unit and the top face of the source unit. The third arm has, at the end of the protective unit remote from the stand element, a protective shield for supporting the patient's head. The third arm can initially follow the shape of the source unit and then be continued therebeyond, so that the protective shield is formed, or can be aligned, at head height for the patient. The protective shield can be designed in particular such that it remains in a fixed position during the entire acquisition or examination, and the head can remain resting against the protective shield during the entire acquisition or examination. This can advantageously protect the patient's head in particular from collisions when the source unit is moving. Advantageously, fears of a collision can be reduced advantageously, allowing a more agreeable examination.

The protective unit can be improved advantageously in particular with regard to the hardware interface, the collision protection and additional functions. Advantageously, the protective unit being attached independently of the source unit can simplify operation of the mammography system. Advantageously, the head can be better protected against collisions, and the fear of such collisions can be reduced.

In an embodiment, the mammography system has a stand unit, a source unit and a protective unit. The stand unit is designed to locate the mammography system on the floor. The L-shaped source unit has one arm rotatably mounted on a front face of the stand unit, and the other arm protrudes substantially perpendicularly, with the result that an X-ray source is located at the end of the source unit remote from the stand unit. The X-ray detector is located on the front face of the stand unit. The X-ray detector can be mounted such that it can rotate, in particular independently, with respect to the stand unit or the source unit. The, in particular substantially U-shaped, protective unit can comprise three arms. The stand unit can comprise the first arm. The first arm can be attached to a rear face or a front face of, or inside, the stand unit. The first arm can be attached fixedly or in a rotatably mounted manner, in particular such that t can rotate independently of the source unit. In the event that the stand unit comprises the first arm, the protective unit can be connected to the stand unit in particular fixedly. The second arm can extend along the top face of the source unit in a first operating state. The third arm has, at the end of the protective unit remote from the stand element, a protective shield for supporting the patient's head.

According to one aspect of one or more example embodiments of the present invention, the protective unit is designed to be substantially form-fitting along the rear face of the stand unit and along the source unit in a first operating state. At least from the rotatably mounted attachment on the stand unit to the top face of the source unit and along the top face of the source unit, the protective unit follows the shape of these components. A gap can preferably be created for frictionless movement of the source unit.

According to one aspect of one or more example embodiments of the present invention, the protective unit is stationary in an acquisition state. The protective unit can be stationary during the scan (i.e. during movement of the X-ray source). The protective unit can be able to rotate as a whole. Rotation can be performed automatically according to the set view/task, or else manually by the radiographer. A position such as craniocaudal or mediolateral oblique can be designated as a view. For example, the protective unit can be rotated for an acquisition in a mediolateral oblique position. This position can describe an orientation of the protective unit in a second operating state.

According to one aspect of one or more example embodiments of the present invention, the protective shield is adjustable to suit the object under examination. The contact surface with the patient can be displaceable and can be adjusted according to the patient's size or according to the view/task. The relevant adjustment can be made automatically based on the set view/set task.

The contact surface with the patient can be designed to pivot away. The protective unit can be designed to pivot away as a whole. The contact surface with the patient is removable and, if applicable, replaceable. For example, this allows an opaque protective shield to be selected, for instance for a biopsy.

It is possible to check that the protective unit is working correctly, for instance by fitting light guides, which bring about suitable lighting for the right installation. In different embodiments, the protective unit can be attached to the object table, to the stand unit or to a stationary spacer ring between the stand unit and the source unit.

The protective unit can be designed to be separable and removable for transportation and packing of the device. The protective unit can comprise an apparatus for attachment to a ceiling (for example of a truck), for instance.

According to one aspect of one or more example embodiments of the present invention, the protective unit comprises sensors for collision protection. The protective unit can contain improved collision protection in addition to its mechanical function of collision protection between patient's head and X-ray source. Sensors, for example based on ultrasound, light, sound, or capacitive sensors can be provided in order to detect a would-be collision before it occurs, and to stop the system automatically. Force sensors can cause a break in the movement of the source unit if the lateral force on the protective unit is too great. This can prevent potential pinching, for instance if there is a finger between protective unit and source unit. If the lateral force on the protective unit becomes too great, the protective unit can pivot away so that pinching can be prevented. The interaction of the sensors and the workflow with existing cameras can allow the output of an early collision warning.

According to one aspect of one or more example embodiments of the present invention, the protective shield pivots away automatically in the event that an applied force exceeds a threshold value. The protective shield can be brought back into the protective position, i.e. back into the original position, for a re-acquisition.

According to one aspect of one or more example embodiments of the present invention, a signal connection is designed to transmit a collision risk from the protective unit to the controller of the X-ray system. The signal connection can be wired or wireless.

The protective unit can have additional functions. The protective unit can contain a mood light in order to create a pleasant atmosphere or to display an operating state. Depending on the operating state, the protective unit, in particular the protective shield, can provide light in another color. The lighting can be formed in the region of the entire protective unit or in a subregion. The protective unit can provide a light field (working light). The working light can be used to illuminate the examination space between the X-ray source and the X-ray detector. In particular, the working light can illuminate the top face of the X-ray detector, making it easier to position the breast. The protective unit can project markers onto the breast after coordinate transfer. The breast can advantageously be positioned more easily and more accurately. The protective unit can be capable of displaying the status of the workflow or of the compression. The protective unit can have a display for this purpose. The protective unit can display via the lighting the status of the workflow or the compression. The working light can be switched on automatically via presence sensors on the protective unit. For example, the working light can be activated automatically as soon as a patient approaches. In addition, the presence sensor can influence the information on the display and switch between information for the patient and for the radiographer. For example, the display can be set to the patient or the radiographer depending on the direction of approach.

The protective unit can contain a display with or without a touch-surface, or consist of such a display. A heart rate measurement and/or a temperature measurement can be performed via the touch-surface. A projector can project information or a mood light onto the protective unit. The patient or the radiographer can be informed of vibrations via a force-feedback function. The protective unit can have automatic or semi-automatic self-cleaning (automatic disinfection). The protective unit can contain an automatic roll-holder so that each time there is a change in patient, the contact surface is replaced (contact surface consists of paper, cloth or film and is stabilized via a solid material without patient contact). The position/orientation of the protective unit is checked via a sensor, and a warning may be output (if the set workflow does not match the position of the face shield).

According to one aspect of one or more example embodiments of the present invention, the protective unit comprises a lighting unit. The lighting unit can comprise a mood light, i.e. atmospheric lighting, lighting according to the operating state, the compression or a workflow status, or work lighting.

According to one aspect of one or more example embodiments of the present invention, the protective unit comprises a display unit and/or input unit. The display unit and/or the input unit can be formed in particular on the protective shield or thereabove in the region of the X-ray source on the source unit.

According to one aspect of one or more example embodiments of the present invention, a presence sensor for distinguishing between object under examination and user is provided. The presence sensor can be formed in particular on the protective shield or thereabove in the region of the X-ray source on the source unit.

According to one aspect of one or more example embodiments of the present invention, the protective unit comprises a cleaning unit. In particular, the cleaning unit can be designed to clean the protective shield. The cleaning unit can provide cleaning via UV light or disinfection agents.

According to one aspect of one or more example embodiments of the present invention, a position sensor of the protective unit is connected to the controller of the X-ray system. A signal relating to the operating state, the compression or the workflow status can be transmitted thereby. For example, this signal can be used to control the lighting.

According to one aspect of one or more example embodiments of the present invention, the protective shield has a convex curvature toward the object under examination. The protective shield can thereby conform substantially to the shape of the head. The comfort of the patient can advantageously be increased. It is advantageously possible to prevent the head slipping sideways away from the protective shield.

According to one aspect of one or more example embodiments of the present invention, the shape of the protective shield conforms to the shape of the head.

According to one aspect of one or more example embodiments of the present invention, the protective shield comprises a temperature sensor and/or a heart rate sensor. A status of the patient can advantageously be determined. The status can relate to a stress level, in particular as regards the heart rate sensor. The radiographer can be informed of the measured values from the temperature sensor and/or from the heart rate sensor, for instance via a display unit or even audibly or visually, in particular via the lighting unit. The measured values from the temperature sensor and/or from the heart rate sensor can be stored jointly with the acquisition.

In particular, the protective shield can have a novel shape. The curvature of the protective shield toward the patient can be designed such that the woman can support her head as in a bowl. The woman can lean her head past the protective shield only with difficulty, and her hair should not get into the beam path or into the tube movement. The curvature and width of the protective shield can be designed such that the woman can rest her head comfortably without feeling constricted. The protective shield can either be taken out or moved away, for instance for examinations for which it is not needed. The outward curvature lets the woman rest her head safely and comfortably. The advantage of this protective shield is that it is stationary and hence can be used for all examinations, even for oblique acquisitions, without the need for further protective shields.

FIG. 1 shows an exemplary embodiment of an X-ray system 1 according to the invention in a first embodiment. The mammography system 1 has a stand unit 2 for locating the mammography system 1 on the floor. The mammography system 1 also has an L-shaped source unit 3, one arm 4 of which is connected to the X-ray detector 20 in a rotatably mounted manner on a front face of the stand unit 2, and the other arm 5 protrudes substantially perpendicularly, with the result that an X-ray source 6 is located at the end of the source unit 3 remote from the stand element or the stand unit. The mammography system 1 further has a substantially U-shaped protective unit 7, the first arm 9 of which is attached to a rear face of the stand unit 2 in a rotatably mounted manner such that it can rotate independently of the source unit 3, the second arm 10 extends along the top face of the source unit 3 in a first operating state, and the third arm 11 has, at the end of the protective unit 7 remote from the stand element or the stand unit 2, a protective shield 8 for supporting the patient's head.

The protective unit 7 is designed to be substantially form-fitting along the rear face of the stand unit 2 and along the source unit 3 in a first operating state. The protective unit 7 is stationary in an acquisition state.

The mammography system 1 is designed to be located and fastened on the floor, in particular of an examination room. The stand unit 2 stands on the floor. On the stand unit 2 is located an L-shaped source unit 3. The source unit 3 is connected to the stand unit 2 in a rotatably mounted manner so as to facilitate full-field digital mammography acquisitions from different acquisition angles, for instance cranio-caudal or mediolateral oblique, and tomosynthesis acquisitions. The source unit 3 is L-shaped. One arm 4 runs substantially parallel to the front of the stand unit 2 and comprises the rotatably mounted connection to the stand unit 2. Also located on the stand unit 2 is an X-ray detector 20, which is also designed to be rotatably mounted, namely with respect to both the source unit 3 and the stand unit 2. Hence the source unit 3 and the X-ray detector 20 can be rotated independently of one another with respect to the stand unit 2. The breast can be arranged in particular on a housing surface of the X-ray detector 20. The breast can be arranged as an object under examination between the X-ray source 6 and the X-ray detector 20. The X-ray detector 20 can be stationary in particular during the X-ray acquisition. For a full-field digital mammography acquisition, the X-ray source 6 can be located opposite the X-ray detector 20 so that the central ray of the X-ray source 6 strikes the detection surface of the X-ray detector 20 at right angles. For a tomosynthesis acquisition, the X-ray source 6 can be rotated via the source unit 3, in particular in an angle range of 15 to 50 degrees. For the central projection, the central ray can strike the detection surface at right angles.

The protective unit 7 is U-shaped. The protective unit 7 comprises three arms 9, 10, 11. The first arm 9 is attached to the stand unit 2 in a rotatably mounted manner such that it can rotate independently of the source unit 3. The first arm 9 is preferably attached to a rear face of the stand unit 2 in a rotatably or pivotably mounted manner. The second arm 10 extends along the top face of the source unit 3 in a first operating state. Thus the first arm 9 and the second arm 10 can follow the shape of the rear face of the stand unit 2 and the top face of the source unit 3. The third arm 11 has, at the end of the protective unit 7 remote from the stand unit 2, a protective shield 8 for supporting the patient's head. The third arm 11 can initially follow the shape of the source unit 3 and then be continued therebeyond, so that the protective shield 8 is formed, or can be aligned, at head height for the patient. The protective shield 8 can be designed in particular such that it remains in a fixed position during the entire acquisition or examination, and the head can remain resting against the protective shield 8 during the entire acquisition or examination.

The protective unit 7 is designed to be substantially form-fitting along the rear face of the stand unit 2 and along the source unit 3 in a first operating state. At least from the rotatably mounted attachment on the stand unit 2 to the top face of the source unit 3 and along the top face of the source unit 3, the protective unit 7 follows the shape of these components. A gap can preferably be created for frictionless movement of the source unit 3.

The protective unit 7 is stationary in an acquisition state. The protective unit 7 can be stationary during the scan (i.e. during movement of the X-ray source). The protective unit 7 can rotate as a whole. Rotation can be performed automatically according to the set view/task, or else manually by the radiographer. A position such as craniocaudal or mediolateral oblique can be designated a view. For example, the protective unit 7 can be rotated for an acquisition in a mediolateral oblique position. This position can describe an orientation of the protective unit 7 in a second operating state.

The protective shield 8 is adjustable to suit the object under examination. The contact surface with the patient can be displaceable and can be adjusted according to the patient's size or according to the view/task. The relevant adjustment can be made automatically based on the set view/set task.

The contact surface with the patient can be designed to pivot away. The protective unit 7 can be designed to pivot away as a whole. The contact surface with the patient is removable and, if applicable, replaceable. For example, this allows an opaque protective shield 8 to be selected, for instance for a biopsy.

It is possible to check that the protective unit 7 is working correctly, for instance by fitting light guides, which bring about suitable lighting for the right installation. In different embodiments, the protective unit 7 can be attached to the object table, to the stand unit 2 or to a stationary spacer ring between the stand unit 2 and the source unit 3.

The protective unit 7 can be designed to be separable and removable for transportation and packing of the device. The protective unit 7 can comprise an apparatus for instance for attachment to a ceiling (for example of a truck).

The protective unit 7 comprises sensors for collision protection. The protective unit 7 can contain improved collision protection in addition to its mechanical function of collision protection between patient's head and X-ray source 6. Sensors, for example based on ultrasound, light, sound, or capacitive sensors can be provided in order to detect a would-be collision before it occurs, and to stop the system automatically. Force sensors can cause a break in the movement of the source unit 3 if the lateral force on the protective unit 7 is too great. This can prevent potential pinching, for instance if there is a finger between protective unit 7 and source unit 3. If the lateral force on the protective unit 7 becomes too great, the protective unit 7 can pivot away so that pinching can be prevented. The interaction of the sensors and the workflow with existing cameras can allow the output of an early collision warning.

The protective shield 8 pivots away automatically in the event that an applied force exceeds a threshold value. The protective shield 8 can be brought back into the protective position, i.e. back into the original position, for a re-acquisition.

A signal connection is designed to transmit a collision risk from the protective unit 7 to the controller of the X-ray system. The signal connection can be wired or wireless.

The protective unit 7 can have additional functions. The protective unit 7 can contain a mood light in order to create a pleasant atmosphere or to display an operating state. Depending on the operating state, the protective unit 7, in particular the protective shield 8, can provide light in another color. The lighting can be formed in the region of the entire protective unit 7 or in a subregion. The protective unit 7 can provide a light field (working light). The working light can be used to illuminate the examination space between the X-ray source 6 and the X-ray detector 20. In particular, the working light can illuminate the top face of the X-ray detector 20, making it easier to position the breast. The protective unit 7 can project markers onto the breast after coordinate transfer. The breast can advantageously be positioned more easily and more accurately. The protective unit 7 can be capable of displaying the status of the workflow or of the compression. The protective unit 7 can have a display for this purpose. Via the lighting, the protective unit 7 can display the status of the workflow or the compression. The working light can be switched on automatically via presence sensors on the protective unit 7. For example, the working light can be activated automatically as soon as a patient approaches. In addition, the presence sensor can influence the information on the display and switch between information for the patient and for the radiographer. For example, the display can be set to the patient or the radiographer depending on the direction of approach. The protective unit 7 can contain a display with or without a touch-surface, or consist of such a display. A heart rate measurement and/or a temperature measurement can be performed via the touch-surface. A projector can project information or a mood light onto the protective unit 7. The patient or the radiographer can be informed of vibrations via a force-feedback function. The protective unit 7 can have automatic or semi-automatic self-cleaning (automatic disinfection). The protective unit 7 can contain an automatic roll-holder so that each time there is a change in patient, the contact surface is replaced (contact surface consists of paper, cloth or film and is stabilized via a solid material without patient contact). The position/orientation of the protective unit 7 is checked via a sensor, and a warning may be output (if the set workflow does not match the position of the face shield).

The protective unit 7 comprises a lighting unit. The lighting unit can comprise a mood light, i.e. atmospheric lighting, lighting according to the operating state, the compression or a workflow status, or work lighting.

The protective unit 7 comprises a display unit and/or input unit. The display unit and/or the input unit can be formed in particular on the protective shield 8 or thereabove in the region of the X-ray source 6 on the source unit 3.

A presence sensor for distinguishing between object under examination and user is provided. The presence sensor can be formed in particular on the protective shield 8 or thereabove in the region of the X-ray source 6 on the source unit 3.

The protective unit 7 comprises a cleaning unit. In particular, the cleaning unit can be designed to clean the protective shield 8. The cleaning unit can provide cleaning via UV light or disinfection agents.

A position sensor of the protective unit 7 is connected to the controller of the X-ray system or of the mammography system 1. A signal relating to the operating state, the compression or the workflow status can be transmitted thereby. For example, this signal can be used to control the lighting.

The protective shield 8 has a convex curvature toward the object under examination. The protective shield 8 can thereby conform substantially to the shape of the head. The shape of the protective shield 8 conforms to the shape of the head.

The protective shield 8 comprises a temperature sensor and/or a heart rate sensor. The status can relate to a stress level, in particular as regards the heart rate sensor. The radiographer can be informed of the measured values from the temperature sensor and/or from the heart rate sensor, for instance via a display unit or even audibly or visually, in particular via the lighting unit. The measured values from the temperature sensor and/or from the heart rate sensor can be stored jointly with the acquisition.

In particular, the protective shield 8 can have a novel shape. The curvature of the protective shield 8 toward the patient can be designed such that the woman can support her head as in a bowl. The woman can lean her head past the protective shield 8 only with difficulty, and her hair should not get into the beam path or into the tube movement. The curvature and width of the protective shield 8 can be designed such that the woman can rest her head comfortably without feeling constricted. The protective shield 8 can either be taken out or moved away, for instance for examinations for which it is not needed. The outward curvature lets the woman rest her head safely and comfortably. The advantage of this protective shield 8 is that it is stationary and hence can be used for all examinations, even for oblique acquisitions, without the need for further protective shields 8.

Figure 2:
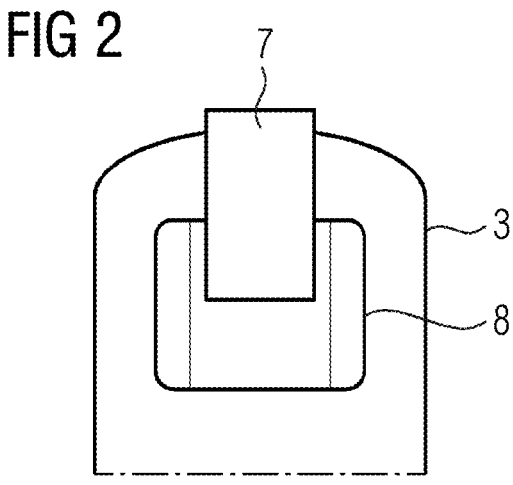
FIG. 2 shows schematically a representation of an X-ray system according to the invention in a second embodiment.
Figure 3:
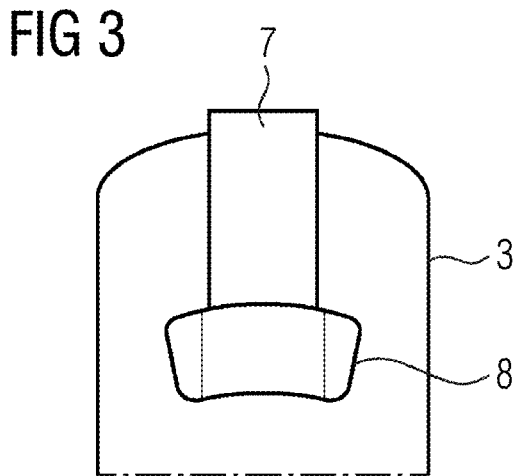
FIG. 3 shows schematically a representation of an X-ray system according to the invention in a third embodiment.
Figure 4:
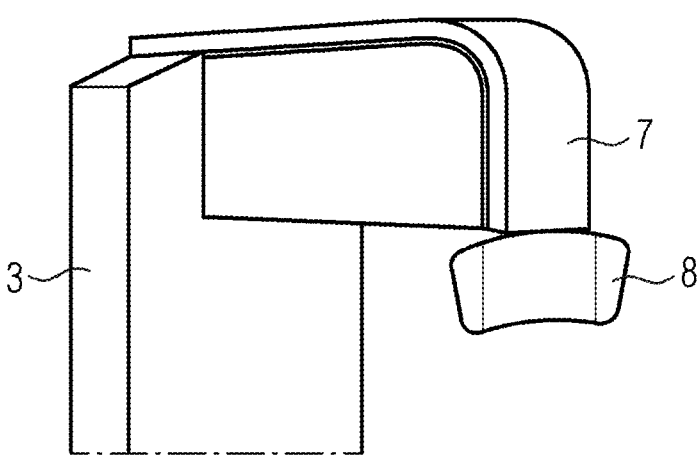
FIG. 4 shows schematically a representation of an X-ray system according to the invention in a fourth embodiment.
Figure 5:
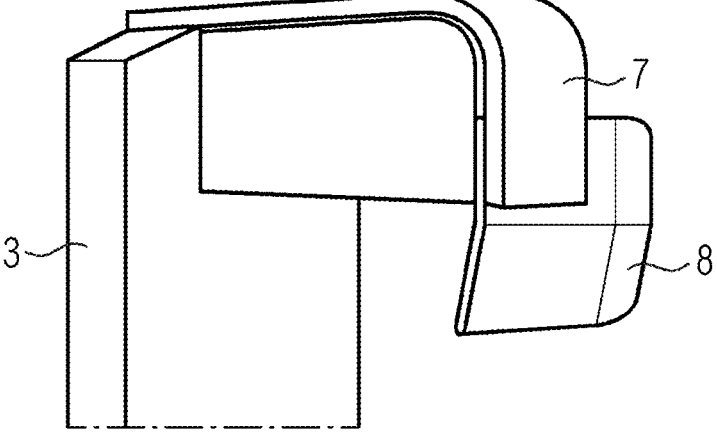
FIG. 5 shows schematically a representation of an X-ray system according to the invention in a fifth embodiment.
Figure 6:
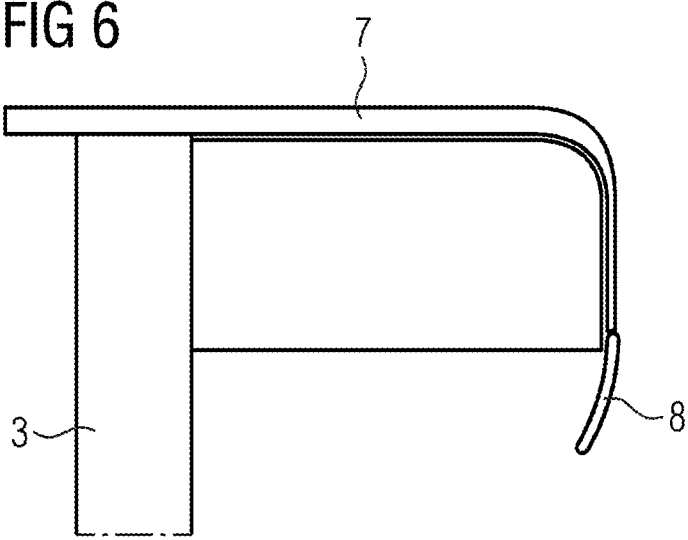
FIG. 6 shows schematically a representation of an X-ray system according to the invention in a sixth embodiment.
Figure 7:
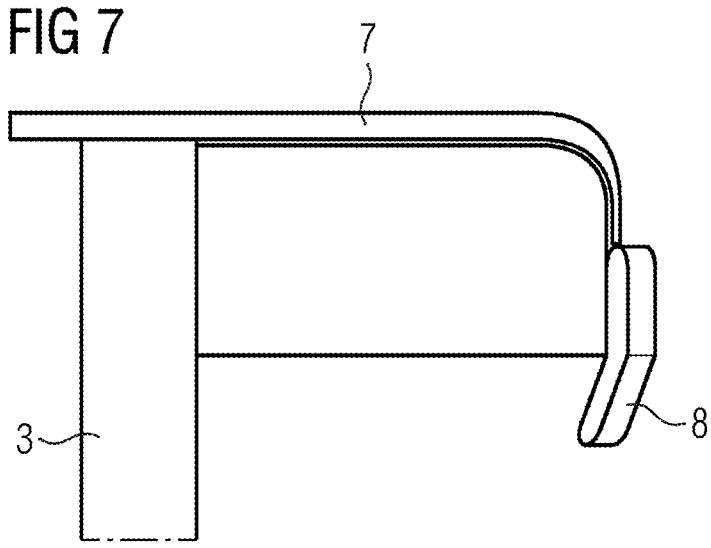
FIG. 7 shows schematically a representation of an X-ray system according to the invention in a seventh embodiment.

FIGS. 2 to 7 show exemplary embodiments of an X-ray system or mammography system according to the invention in a second to seventh embodiment. The protective shield 8 has a convex curvature toward the object under examination. The shape of the protective shield 8 conforms to the shape of the head. FIGS. 2, 5 and 7 show different perspectives of a first exemplary embodiment of the protective shield 8. FIGS. 3, 4 and 6 show different perspectives of a second exemplary embodiment of the protective shield 8.

Although the invention has been illustrated in greater detail using the preferred exemplary embodiment, the invention is not limited by the disclosed examples, and a person skilled in the art can derive other variations therefrom without departing from the scope of protection of the invention.

The invention claimed is:

1. A mammography system comprising:
a stand unit for locating the mammography system on a floor;
an L-shaped source unit, the L-shaped source unit including an arm connected to an X-ray detector in a rotatably mounted manner on a front face of the stand unit, and another arm of the L-shaped source unit protrudes substantially perpendicularly, an X-ray source being located at an end of the source unit remote from the stand unit; and
a substantially U-shaped protective unit, the substantially U-spaced protective unit including a first arm attached to the stand unit in a rotatably mounted manner such that the protective unit is rotatable independently of the source unit, the substantially U-shaped protective unit including a second arm extending along a top face of the source unit in a first operating state, and the substantially U-shaped protective unit including a third arm having, at the end of the protective unit remote from the stand unit, a protective shield for supporting a head of a patient.

2. The mammography system of claim 1, wherein the protective unit is configured to be substantially form-fitting along a rear face of the stand unit and along the source unit in a first operating state.

3. The mammography system of claim 1, wherein the protective unit is stationary in an acquisition state.

4. The mammography system of claim 1, wherein the protective shield is adjustable to suit an object under examination.

5. The mammography system of claim 1, wherein the protective unit comprises sensors for collision protection.

6. The mammography system of claim 1, wherein the protective shield pivots away automatically in the event that an applied force exceeds a threshold value.

7. The mammography system of claim 5, wherein a signal connection is configured to transmit a collision risk from the protective unit to a controller of the mammography system.

8. The mammography system of claim 1, wherein the protective unit comprises a lighting unit.

9. The mammography system of claim 1, wherein the protective unit comprises at least one of a display unit or input unit.

10. The mammography system claim 9, further comprising:
a presence sensor configured to distinguish between an object under examination and a user.

11. The mammography system of claim 1, wherein the protective unit comprises a cleaning unit.

12. The mammography system of claim 1, wherein a position sensor of the protective unit is connected to a controller of the mammography system.

13. The mammography system of claim 1, wherein the protective shield has a convex curvature toward an object under examination.

14. The mammography system of claim 13, wherein the shape of the protective shield conforms to the head of the patient.

15. The mammography system of claim 1, wherein the protective shield comprises at least one of a temperature sensor or a heart rate sensor.

16. The mammography system of claim 2, wherein the protective unit comprises a cleaning unit.

17. The mammography system of claim 16, wherein a position sensor of the protective unit is connected to a controller of the mammography system.

18. The mammography system of claim 17, wherein the protective shield has a convex curvature toward an object under examination.

19. The mammography system of claim 18, wherein the shape of the protective shield conforms to the head of the patient.

\* \* \* \* \*